United States Patent [19]

Hofmann et al.

[11] 4,427,593

[45] Jan. 24, 1984

[54] PROCESS FOR THE PRODUCTION OF PREDOMINANTLY LINEAR ALIPHATIC CARBOXYLIC ACID ESTERS

[75] Inventors: Peter Hofmann; Wolfgang H. E. Müller, both of Marl, Fed. Rep. of Germany

[73] Assignee: Chemische Werke Hüls AG, Marl, Fed. Rep. of Germany

[21] Appl. No.: 291,915

[22] Filed: Aug. 11, 1981

[30] Foreign Application Priority Data

Sep. 12, 1980 [DE] Fed. Rep. of Germany ....... 3034422

[51] Int. Cl.$^3$ ................................................ C11C 3/02
[52] U.S. Cl. ............................................. 260/410.9 R
[58] Field of Search ................... 260/410.9 R, 410.9 C

[56] References Cited

U.S. PATENT DOCUMENTS

| | | | |
|---|---|---|---|
| 2,522,529 | 9/1950 | Miller et al. | 260/410.9 R |
| 3,328,269 | 6/1967 | Alhoritiere | 260/410.9 R |
| 3,507,891 | 4/1970 | Hearne | 260/410.9 R |
| 3,883,587 | 5/1975 | Isa et al. | 260/410.6 |
| 3,906,016 | 9/1975 | Isa | 260/410.9 R |
| 3,935,228 | 1/1976 | Keblys | 260/410.9 R X |
| 4,041,057 | 8/1977 | Fanning | 260/410.9 R |

OTHER PUBLICATIONS

Peter Hofmann et al., "Hydrocarboxymethylation—An Attractive Route from Olefins to Fatty Acid Esters" Sep. 1980, I & EC Product Research & Development, vol. 19, pp. 330–334.

*Primary Examiner*—Helen M. S. Sneed
*Attorney, Agent, or Firm*—Wells & Wells

[57] ABSTRACT

A process for producing predominantly linear aliphatic carboxylic acid esters by reacting olefins, carbon monoxide and alkanols at elevated pressures and elevated temperatures in the presence of a catalyst consisting of a cobalt compound and a promoter. The promoter is the possibly cobalt-free mixture of substances obtained when a reaction mixture that was prepared by reacting olefins, carbon monoxide and alkanol in the presence of a catalyst consisting of a cobalt compound and pyridine, a non-ortho-substituted alkylpyridine or mixtures at elevated pressure and elevated temperature is reprocessed. This mixture of substances has a higher boiling point than the esters formed as the reaction product and higher than the pyridine, non-ortho-substituted alkylpyridine or mixtures thereof used as the catalytic component.

3 Claims, 1 Drawing Figure

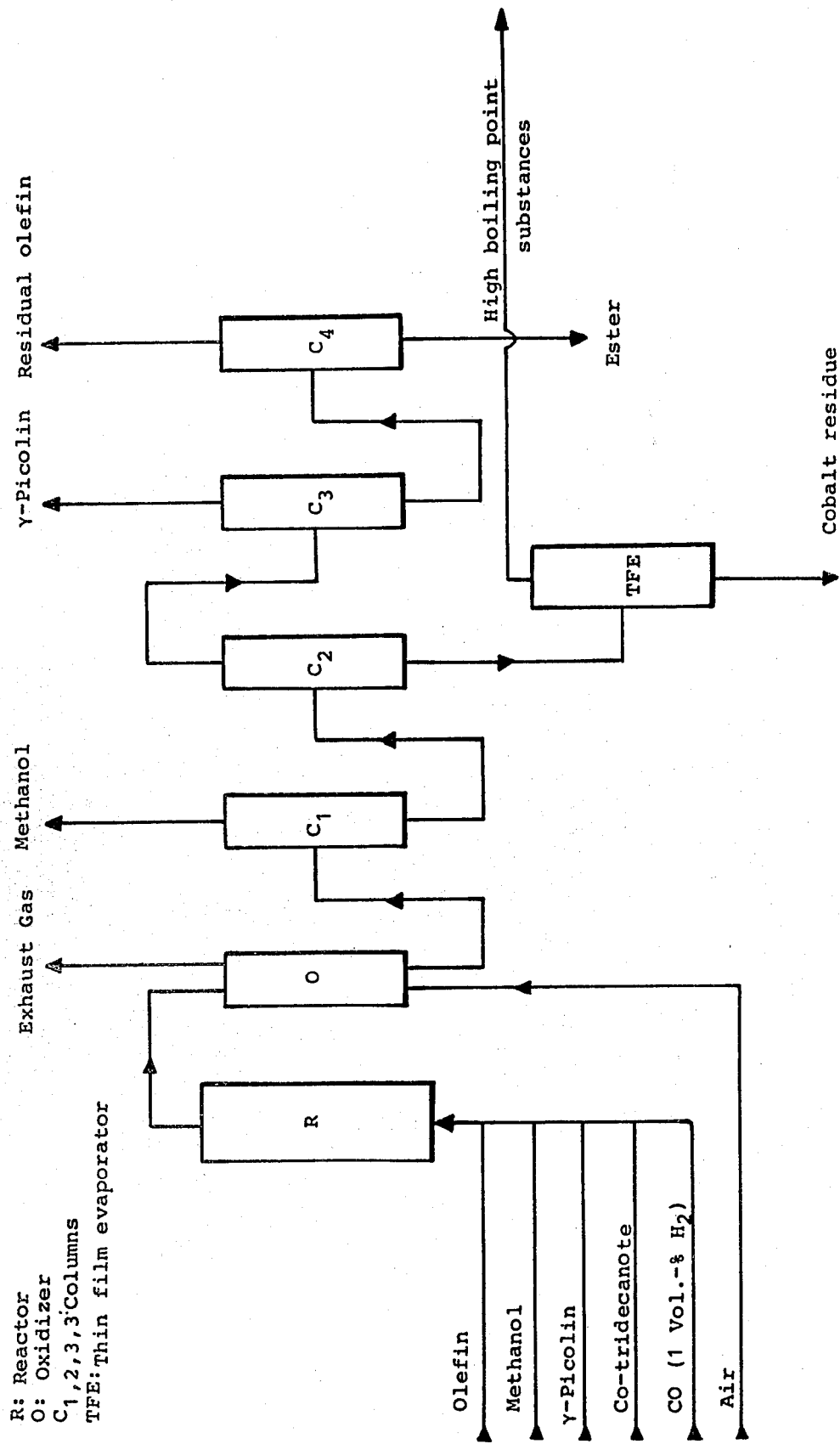

PROCESS FOR THE PRODUCTION OF PREDOMINANTLY LINEAR ALIPHATIC CARBOXYLIC ACID ESTERS

CROSS-REFERENCE TO RELATED APPLICATIONS

Applicants claim priority under 35 USC 119 for application No. P 30 34 422.0, filed Sept. 12, 1980 in the Patent Office of the Federal Republic of Germany.

The disclosure of coinventor Hofmann's copending application, Ser. No. 125,482, filed Feb. 28, 1980 is incorporated herein to show alkoxycarbonylation procedures carried out in the presence of cobalt catalysts and a promotor from the group pyridine, non-ortho-substituted alkylpyridine and mixtures thereof.

Also incorporated herein is coinventor Hofmann's copending application Ser. No. 203,393, filed Nov. 3, 1980 to show that olefins with internal double bonds can be produced by dehydrogenation of paraffins or by chlorination followed by dehydrochlorination of paraffins.

BACKGROUND OF THE INVENTION

The field of the invention is the production of alkyl esters of saturated aliphatic carboxylic acids and the present invention is particularly concerned with reacting olefins with carbon monoxide and alkanol in the presence of a catalyst consisting of a colbalt compound and a promotor selected from pyridine, non-ortho-substituted alkylpyridine or mixtures thereof at elevated pressures and elevated temperatures.

The state of the art of such alkoxycarbonylation reactions may be ascertained by reference to U.S. Pat. Nos. 3,507,891; 3,906,016 and 4,041,057 and the article "Hydrocarboxymethylation—an Attractive Route from Olefins to Fatty Acid Esters?" by Peter Hofmann et al as published in I & EC, Product Research & Development, Vol. 19, Sept. 1980, pp. 330-334, the disclosures of which are incorporated herein.

It is known that by reacting olefins with carbon monoxide and a compound having a replaceable hydrogen atom such as an alkanol in the presence of a catalyst containing a metal of Group VIII of the Periodic Table of elements and possibly a promotor, fatty acid esters can be produced as disclosed in J. Falbe, Synthesen mit Kohlenmonoxid, Springer publishers, Berlin, Heidelberg, New York (1967).

An especially preferred variation of this reaction, which is termed alkoxycarbonylation, is the conversion in the presence of cobalt catalysts. The rate, the selectivity and the yield in linear fatty acid esters of the cobalt reaction can be increased by adding promoters belonging to the pyridine class of compounds. Pyridine itself and also non-ortho-substituted alkylpyridines and mixtures thereof have been found particularly effective.

The application of such promoters suffers from a substantial drawback in that the cost of pyridine and non-ortho-substituted alkylpyridines is relatively high and moreover that these compounds are not always available in the required commercial quantities.

In addition to the costs of the pyridine or the non-ortho-substituted alkylpyridine used as promoter, the economy of a alkoxycarbonylation process is also affected by, among other factors, the achievable ester selectivity and by the usefulness of the by-products.

Whereas the utilization of the paraffin formed as by-product by the olefin hydrogenation, or of the aldehyde formed by hydroformylation as a rule causes no difficulty—paraffins for instance can be used again to prepare the initial olefin, aldehydes can be used just as esters for the production of alcohol or of carboxylic acid—to date no economically significant utilization has been found for the mixture of substances obtained as byproduct, which is of a higher boiling point than the esters formed as reaction product and the pyridine, non-ortho-substituted alkylpyridine or mixtures (high boiling point substances) used as the catalytic component.

In order to prevent an enrichment of these generally high boiling point substances, which in reprocessing by distillation of the alkoxycarbonylation mixture collect together with the catalyst as distillation sump substances, when the reaction is repetitive or continuous, they are either separated by expensive reprocessing methods from the catalytic metal and discarded as disclosed in European published application No. 0 008 024 and German Pat. No. 921,988, or are burned off together with the catalyst as disclosed in British Pat. No. 2,005,652 and U.S. Pat. No. 4,041, 057.

SUMMARY OF THE INVENTION

It is an object of the present invention to create a process for the production of predominantly linear aliphatic carboxylic acid esters, which:

(1) while preserving the advantages of the alkoxycarbonylation employing cobalt and pyridine, pyridine derivatives or mixtures as the catalytic components are free of the high cost of promoter preparation, and (2) permits an economically significant utilization of the high boiling point by-products generated in the alkoxycarbonylation employing cobalt and pyridine, pyridine derivatives or mixtures as catalytic components.

This object is achieved according to the present invention in a process for the production of predominantly linear aliphatic carboxylic acid esters by reacting olefins, carbon monoxide and alkanols at elevated pressures and elevated temperatures in the presence of a catalyst consisting of a cobalt compound and a promotor to form a reaction mixture. The reaction mixture, which is obtained by reacting olefins, carbon monoxide and alkanol in the presence of a catalyst consisting of a cobalt compound and pyridine, a non-ortho-substituted alkylpyridine or a mixture thereof at elevated pressures and elevated temperatures is reprocessed to separate by distillation:

(a) alkanol
(b) promoter
(c) esters formed as the reaction product;
(d) a cobalt residue; and
(e) a high boiling point mixture of substances accumulating as a by-product.

The high boiling point mixture of substances has a boiling point higher than the esters formed as the reaction product and the pyridine, nonortho-substituted alkylpyridine or mixture thereof used as the catalytic component. This high boiling point mixture of substances is fed back or recirculated as the promotor with the cobalt compound in the next alkoxycarbonylation reaction. The high boiling point mixture of substances is defined as having a boiling point range between 115.5° C. and 300° C./0.1 Torr.

Esters formed as the reaction product of the present invention have a boiling point range between 80.5° C.

and 250° C./0.1 Torr. Pyridine, non-ortho-substituted alkylpyridines and mixtures thereof used in the present invention have a boiling point range between 115.5° C. and 250° C./0.1 Torr.

By elevated temperatures is meant about 80° to 300° C., preferably 150° to 200° C.

By elevated pressures is meant carbon monoixde pressures of about 10 to 800, preferably 100 to 300 bars.

BRIEF DESCRIPTION OF THE DRAWING

Submitted herewith is a flow sheet showing the specific embodiment of the present invention as carried out in Example 1.

DESCRIPTION OF THE PREFERRED EMBODIMENTS

The new and unexpected results of the present invention could not be predicted in view of the state of the art where the high boiling point substances were not recognized to have a co-catalytic effect comparable with the conventionally used pyridine promoters.

In principle the process of the present invention can be applied to all alkoxycarbonylation reactions which are carried out in the presence of a cobalt catalyst such as disclosed in U.S. Pat. No. 3,507,891 and U.S. patent application Ser. No. 125,482. Thus, and most of all, the selection of the olefin used is non-critical, that is, both straightchain and branched alpha-olefins and also olefins with an internal double bond can be used. Moreover, olefins with more than one double bond and those with substituents, for instance aryl, cyano, carboximethyl and hydroxyl groups, are suitable.

As a rule, olefins having 2 to 30, preferably 4 to 20 C atoms are used, which can be prepared by methods of the state of the art. For instance alpha-olefins can be prepared by the Ziegler ethylene oligomerization as disclosed in German Pat. No. 878,560 and U.S. Pat. No. 3,310,600, or by wax cracking, and olefins with an internal double bond can be made by catalytic dehydrogenation of paraffins or by chlorinating paraffins and then dehydrochlorinating the chloroparaffins as disclosed in British Pat. No. 1,037,868 and U.S. patent application Ser. No. 203,393.

As regards the last cited method, blends of paraffin, that is, mixtures having different C numbers are used as a rule, whereby the olefins obtained in turn also lack a uniform C number.

Furthermore, all conceivable isomeric forms are obviously also present in these olefin mixtures.

Besides the pure and possibly substituted olefins, it is possible also to use those which contain up to 85% by weight in paraffins. There is a paraffin content because conversions are not complete in the olefin production and the unconverted paraffins are not separated, or the paraffins are only incompletely separated.

Besides the olefin used being non-critical, so also is the kind of the alkanol being reacted with the olefin and carbon monoxide in the process of the present invention. In general alkanols having 1 to 10, preferably 1 to 4 C atoms are used. Typically representative substances from the group of primary alkanols are for instance methanol, ethanol, propanol(1) and butanol-(1). As a rule the amount of the alkanol used is 1 to 10 moles per mole of olefin.

It is moreover immaterial which cobalt compound is used in the alkoxy carbonylation. Cobalt carbonyls, for instance dicobaltoctacarbonyl, are just as suitable as carboxylic acid cobalt salts such as cobalt acetate, cobalt naphthenate and cobalt-2-ethyl hexanoate, and salts of cobalt with inorganic acids such as cobalt nitrate and cobalt sulfate. Preferably those carboxylic acid cobalt salts are used of which the anions correspond to the acid radical of the fatty acid esters formed in the alkoxycarbonylation.

Depending on the kind of olefin being converted, the concentration of the cobalt used as catalyst is in a range of 0.005 to 0.2 gram-atom of cobalt per mole of olefin.

In addition to pyridine alone or in a mixture used with the cobalt compound, the non-ortho-substituted alkylpyridines include 3-picoline, 4-picoline, 3,4-dimethylpyridine, and 3,5-dimethylpyridine and 3-ethylpyridine and 4-ethylpyridine.

Lastly, the conditions of reaction in which the alkoxycarbonylation is carried out are of no significance for the process of the present invention. As a rule the alkoxycarbonylation procedures are implemented at temperatures of 80° to 300°, preferably 150° to 200° C. and at carbon monoxide pressures of 10 to 800, preferably 100 to 300 bars.

What is process-critical for the present process, however, is the use of a promoter (cocatalyst) which collects as a cobalt-free or nearly cobalt-free (less than 1 ppm by weight) mixture of substances in the reprocessing of specific alkoxycarbonylation mixtures and which is of a higher boiling point than the esters contained in these alkoxycarbonylation mixtures and a higher boiling point than the pyridine, non-ortho-substituted alkylpridine or mixture used as the catalytic component in these alkoxycarbonylation reactions. The alkoxycarbonylation mixtures providing the mixture of substances usable as the promoters of the present invention and possibly free of cobalt are obtained by reacting olefins, carbon monoxide and alkanol in the presence of a catalyst consisting of a cobalt compound and pyridine, non-ortho-substituted alkylpyridine or mixtures thereof at elevated pressure and elevated temperature. Such a reaction is subjected to no particular restrictions regarding the selection of the initial materials, the reagent ratios and the conditions of reaction. The requirements which must be met in general for the methods disclosed in U.S. Pat. No. 3,507,891 and U.S. patent application Ser. No. 125,482 also apply to the present invention. These requirements essentially correspond to the conditions which must be met in the process of the present invention.

The process of the present invention furthermore is non-critical as regards the manner in which the high boiling point substances used as promotor(s) are separated from the alkoxycarbonylation mixture obtained for instance by a method as disclosed in U.S. Pat. No. 3,507,891 and U.S. patent application Ser. No. 125,482. Thus, these high boiling point substances are extracted from such cobalt residue as there is for instance after removal by distillation of unconverted input materials and of the esters obtained as reaction products. To that end, available extraction methods among others, are disclosed in European published application No. 0 008 024 and U.S. patent application Ser. No. 203,393. Also useful distillation methods are, for instance, those using a thin film evaporator.

However, it is also possible to leave the high boiling point substances in the cobalt residue and to use the residue as a whole as the catalytic system (cobalt compound + promoter) in the process of the present invention.

Whereas in the alkoxycarbonylation methods of, for instance, U.S. Pat. No. 3,507,891 and U.S. patent application Ser. No. 125,482 use is made of specific promoters (pyridine, non-ortho-substituted alkylpyridines and mixtures) and therefore also specific promoter/cobalt ratios are set, this is impossible when the high boiling point substances of the present invention are used as promoters since these substances consist of a plurality of unknown compounds. As regards alkoxycarbonylation methods for instance according to U.S. Pat. No. 3,507,891 and U.S. patent application Ser. No. 125,482, as a rule promoter/cobalt ratios of 3/1 to 25/1 (promoter in moles, cobalt in gram-atom) are used. The quantitative ratios to be observed in the process of the present invention on the other hand cannot be specified at once beforehand. However, they can be easily ascertained by the few trial-and-error methods. Appropriately, this is done by performing sample reactions under the conditions of the process of the present invention with various amounts of the high boiling substances. When alpha-olefins are reacted, it is recommended to operate typically with that amount of high boiling point substance for which a maximum conversion is observed. The maximum rate of reaction in general is accompanied in alphaolefins by optimal values of selectivity and linearity. When using olefins with an internal double bond, there will not be in general such simple relationships between the desired target values, and therefore in such instances the amount of high boiling point substances is obtained as a compromise between the rate of reaction, the selectivity and the linearity as a function of the amount of high boiling point substances used per gram-atom of cobalt.

In general, the high boiling point substances are used in an amount of about 2 to 20, preferably 5 to 15 kg per gram-atom of cobalt.

Obviously it is equally possible to use pyridine, non-ortho-substituted alkylpyridines and mixtures thereof, together with the high boiling point substances as co-promoters, where 1 mole of pyridine or of non-ortho-substituted alkylpyridine corresponds to an amount of about 0.2 and 1.5 kg of high boiling point substances regarding the promoter activity.

Using the process of the present invention, which is discussed further below in relation to the examples, it becomes possible to prepare aliphatic carboxylic acid esters with a linearity of a similar magnitude as when pyridine, non-ortho-substituted alkylpyridine or mixtures thereof are used as the promoter.

The carboxylic acid esters obtained by the process of the present invention are valuable intermediate products products in the manufacture for instance of surfactants and softeners.

EXAMPLE 1

(A) Preparing the high boiling point substance used as the promoter

A mixture of the following input materials
1 mole of n-dodecene (isomeric mixture with a dodecene-(1) proportion less than 1% by weight)
2 moles of methanol
0.3 moles of gamma-picoline
0.03 gram-atom of cobalt (in the form of a mixture of Co-tridecanoate/tridecanoic acid with a cobalt content of 10%)

is continuously pumped into an agitated autoclave where it is made to react under the following conditions:
reaction temperature: 185° C.
CO hot pressure (CO contains 1% by volume of $H_2$): 180 bars
Dwell time: 1.6 hrs.

The agitated autoclave discharge is continuously fed into the top of a 1 m long trickling tower filled with $8 \times 8$ mm Raschig rings and is treated with air in counterflow under the following conditions:
temperature of reaction: 40° C.
pressure: 1 bar
liquid flow rate: 260 ml/$cm^2$.h
air per liter of reaction output: 50 liters The reaction output treated with air is continuously separated in a stepwise manner in a distillation cascade into unconverted methanol, gamma-picoline, unconverted olefin and a mixture of esters formed as reaction products and a sump product containing the cobalt used as catalyst and also a high boiling point substance accumulating as a byproduct. The high boiling point substance accumulates together with the cobalt used as catalyst as the sump product of column $C_2$ (see flow sheet).

This sump product is concentrated by distillation in a falling film evaporator operating at the following conditions:
pressure at the transfer point: 20 mbar
heater temperature: 241° C.
rotor speed: 900 rpm to such an extent that the residue so obtained has a cobalt content of 10%. The amount of high boiling point substance distilled off at 229° C. and referred to the mixture of tridecanoic acid methylester formed as the reaction product amounts to 1.9%.

B. Using the high boiling point Substance as the Promoter

A mixture of the following input materials
1 mole of n-dodecene (isomeric mixture with a dodecene-(1) proportion less than 1% by weight)
2 moles of methanol
0.03 gram-atoms of cobalt (in the form of 10% Co-tridecanoate
420 g of a high boiling point substance (prepared per Example 1A)

are reacted in a 2-liter agitated autoclave under the following conditions: p1 reaction temperature: 185° C.
CO hot pressure (CO with 1% by vol of $H_2$): 180 bars
duration of reaction: 3 hrs.

The gas chromatographic analysis of the reaction mixture shows the following:
olefin conversion: 72%
selectivity: 95%
proportion of linear tridecanoic acid methyl ester: 74%.

EXAMPLE 2

Example 1 is repeated except that the reaction in the presence of the high boiling substance as the promotor takes place with octene-(1) as input olefin at a temperature of 160° C. and a pressure of 270 bars. The gas-chromatographic analysis of the reaction mixture shows:
olefin conversion: 78%
selectivity: 97%
proportion of linear nonanoic acid methyl ester: 78%.

EXAMPLES 3 THROUGH 5

Preparing the high boiling point substance used as promoter for Examples 3-5

Maintaining the conditions of reaction and reprocessing described under Example (1A) and while constantly feeding back the cobalt residue freed from the high boiling point substances as catalyst and by using again the unconverted input substances, the continuous reaction described in Example 1A) is repeated until the catalyst has been circulated 10 times. The high boiling point substances accumulating after catalyst circulations (1.8% referred to the mixture of tridecanoic acid methyl esters formed as the reaction product) are used as promoter under the conditions listed in Table 1.

EXAMPLES 6 THROUGH 8

The Examples 3 through 5 are repeated except that gamma-picoline is replaced as promoter by the same molar amount of pyridine in the process for preparing the high boiling point substance (Table 1).

TABLE 1

| Example | Olefin | Alkanol | Co-Tridecanoate (10%) | Promoter | |
|---|---|---|---|---|---|
| 3 | 1 mol n-dodecene[1] | 2 mol CH$_3$OH | 0.03 mol | 210 g* | |
| 4 | 1 mol octene-(1) | 2 mol CH$_3$OH | 0.015 mol | 210 g* | |
| 5 | 1 mol octene-(1) | 2 mol CH$_3$OH | 0.015 mol | 105 g* +14 g | γ-picoline |
| 6 | 1 mol n-dodecene[1] | 2 mol CH$_3$OH | 0.03 mol | 210 g* | |
| 7 | 1 mol octene-(1) | 2 mol CH$_3$OH | 0.015 mol | 210 g* | |
| 8 | 1 mol octene-(1) | 2 mol CH$_3$OH | 0.015 mol | 105 g* +14 g | γ-picoline |

| Example | Temperature [°C.] | Pressure [bar] | Reaction time [hr] | Conversion [%] | Selectivity [%] | Linearity [%] |
|---|---|---|---|---|---|---|
| 3 | 185 | 180 | 3 | 75 | 95 | 75 |
| 4 | 160 | 270 | 3 | 82 | 97 | 82 |
| 5 | 160 | 270 | 3 | 80 | 96 | 83 |
| 6 | 185 | 180 | 3 | 73 | 94 | 74 |
| 7 | 160 | 270 | 3 | 81 | 97 | 80 |
| 8 | 160 | 270 | 3 | 82 | 97 | 83 |

[1]isomeric mixture with dodecene-(1) proportion less than 1% by weight
*high boiling point substance

We claim:

1. In a process for the production of predominantly linear aliphatic carboxylic acid esters by reacting olefins, carbon monoxide and alkanols at elevated pressures and elevated temperatures in the presence of a catalyst consisting of a cobalt compound and a promoter, comprising:

(A) reacting olefins, carbon monoxide and alkanols in the presence of a catalyst consisting of a cobalt compound and pyridine, a non-ortho-substituted alkylpyridine or a mixture thereof at elevated pressures and elevated temperatures to form a reaction mixture;

(B) separating said reaction mixture into the following fractions:
  (a) esters formed as a reaction product;
  (b) said pyridine, non-ortho-substituted alkylpyridine, or mixture thereof;
  (c) unreacted olefins, carbon monoxide and alkanols; and
  (d) a cobalt sump product; the improvement comprising
  (e) separating a cobalt free mixture of high boiling point substances having a higher boiling point than said esters formed as the reaction product and higher than said pyridine, non-ortho-substituted alkylpyridine or mixtures thereof used as the catalytic component; and (C) using said cobalt free mixture of high boiling point substances as promotor in said process for the production of predominantly linear aliphatic carboxylic acid esters.

2. The process of claim 1, wherein said cobalt free mixture of substances is used as a copromoter with said pyridine, nonortho-substituted alkylpyridine or mixture thereof.

3. The process of claim 1, wherein said cobalt free mixture of substances has a boiling point of 115.5° to 300° C. at 0.1 Torr pressure.

* * * * *